(12) United States Patent
McGreevy et al.

(10) Patent No.: US 8,140,141 B2
(45) Date of Patent: Mar. 20, 2012

(54) DEVICES AND METHODS FOR FLUORESCENT INSPECTION AND/OR REMOVAL OF MATERIAL IN A SAMPLE

(75) Inventors: James McGreevy, Salt Lake City, UT (US); Charles B. Grissom, Salt Lake City, UT (US); Ronald M. Jones, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 1614 days.

(21) Appl. No.: 11/436,878

(22) Filed: May 17, 2006

(65) Prior Publication Data

US 2007/0269837 A1 Nov. 22, 2007

(51) Int. Cl.
*A61B 5/00* (2006.01)
(52) U.S. Cl. .......... 600/317; 600/300; 600/310; 607/88
(58) Field of Classification Search .............. 607/88–93; 606/10–12; 600/101–104, 108–112, 300, 600/309, 310, 317; 424/9.1, 9.6; 128/905
See application file for complete search history.

(56) References Cited

U.S. PATENT DOCUMENTS

| | | | |
|---|---|---|---|
| 4,355,018 A | 10/1982 | Hansen et al. | |
| 4,465,775 A | 8/1984 | Houts | |
| 4,680,273 A | 7/1987 | Herbert | |
| 4,930,516 A * | 6/1990 | Alfano et al. | 600/477 |
| 5,062,431 A * | 11/1991 | Potter | 600/478 |
| 5,104,815 A | 4/1992 | Garner et al. | |
| 5,187,107 A | 2/1993 | Watkins et al. | |
| 5,227,311 A | 7/1993 | Kuemmerle et al. | |
| 5,341,240 A | 8/1994 | Broome | |
| 5,421,337 A | 6/1995 | Richards-Kortum et al. | |
| 5,590,660 A * | 1/1997 | MacAulay et al. | 600/478 |
| 5,614,394 A | 3/1997 | Hoyle et al. | |
| 5,716,595 A | 2/1998 | Goldenberg | |
| 5,827,190 A * | 10/1998 | Palcic et al. | 600/476 |
| 5,928,627 A | 7/1999 | Kiefer et al. | |
| 6,096,289 A | 8/2000 | Goldenberg | |
| 6,096,290 A | 8/2000 | Collins et al. | |
| 6,363,940 B1 | 4/2002 | Krag | |
| 6,387,350 B2 | 5/2002 | Goldenberg | |
| 6,571,118 B1 | 5/2003 | Utzinger et al. | |
| 2004/0082863 A1 | 4/2004 | McGreevy et al. | |
| 2004/0161804 A1 | 8/2004 | McCash et al. | |
| 2005/0249667 A1 | 11/2005 | Tuszynski et al. | |
| 2007/0015963 A1 * | 1/2007 | Fengler et al. | 600/109 |

* cited by examiner

*Primary Examiner* — Ahmed Farah
(74) *Attorney, Agent, or Firm* — Rothwell, Figg, Ernst & Manbeck P.C.

(57) ABSTRACT

An apparatus is provided that includes a light-emitting component, a light-detecting component, a lock-in amplifier, a frequency generator that is operatively linked to the lock-in amplifier and the light-emitting component, a speaker capable of emitting an audio signal wherein the output audio signal varies depending on the detected fluorescence in the sample, and a visible output of relative fluorescent intensity where the visible output varies depending on the detected fluorescence in the sample. The apparatus may also include a laser that is operatively coupled to the lock-in amplifier through a control switch, and focusing lens or an additional type of filter such as an interference filter, a short-pass filter, a notch filter, a long-pass filter or an infrared filter. The apparatus may be used to identify and/or to remove fluorescent or non-fluorescent material from a sample. Associated methods are also disclosed.

14 Claims, 3 Drawing Sheets

DEVICES AND METHODS FOR FLUORESCENT INSPECTION AND/OR REMOVAL OF MATERIAL IN A SAMPLE

TECHNICAL FIELD

The present disclosure relates to systems, devices and methods for exciting fluorescent, phosphorescent, or luminescent molecules with light from a light source and detecting the relative fluorescent, phosphorescent, or luminescent light intensity emitted from the fluorescent, phosphorescent, or luminescent molecule. According to certain embodiments, the relative emitted light intensity may be used to control a laser, an electrocautery device or scalpel, or ultrasonic cutting or ablation device to aid in, or cause, the destruction or removal of either light-emitting or non-light-emitting material once identified. According to certain embodiments, fluorescent, phosphorescent, or luminescent conjugates or chemical analogues of cobalamin (sometimes referred to herein as CobalaFluors) can be used with the disclosed devices and methods. The fluorescent, phosphorescent, or luminescent cobalamin conjugates comprise a fluorescent, phosphorescent, luminescent or light-producing compound that is covalently linked or otherwise complexed to cobalamin or a closely related analogue thereof. These fluorescent cobalamin conjugates can be used as diagnostic and prognostic markers (a) to distinguish cancer cells and tissues from healthy cells and tissues, including the mapping and imaging of lymphatic vessels and lymph nodes, and identifying lymph nodes that contain cancer cells, (b) to determine if an individual can reasonably be expected to respond positively to chemotherapy using cobalamin-based therapeutic bioconjugates.

BACKGROUND OF THE INVENTION

Rapidly dividing cells require cobalamin as a cofactor for the enzyme methionine synthase to support one-carbon metabolism prior to DNA replication. In acute promyelocytic leukemia, a 3-26 fold increase in the unsaturated $B_{12}$ binding capacity of blood is observed, due to an increase in the concentration of the $B_{12}$ binding proteins transcobalamin and haptocorrin. Some patients with solid tumors also exhibit a significant increase in the circulating levels of transcobalamin and haptocorrin. The increase in unsaturated serum cobalamin binding capacity corresponds to the increased uptake of cobalamin by rapidly dividing cells. Tumors sequester sufficient cobalamin for diagnostic imaging purposes if a gamma-emitting radionuclide, such as 111In, is attached to cobalamin through the octadentate chelator diethylenetriaminepentaacetic acid (DTPA). This has been demonstrated in mice with an implanted fibrosarcoma, as well as in humans with breast cancer, and in tumors of the prostate, lung and brain.

In the sentinel lymph node concept for melanoma and breast cancer surgery, a dye or radionuclide is injected into the tissue around the tumor to identify the first lymph node that drains the tumor and its surrounding tissue. This node is termed the sentinel node, and it is removed for diagnostic tests to determine the extent of metastasis beyond the primary tumor. This procedure is controversial, as it fails to detect metastatic disease in about 12% of patients. The dye or radionuclide that is injected is not specific for cancer cells, but merely identifies for the surgeon the primary lymph node that drains the region of the tumor. The high false-negative rate should be improved dramatically by using a fluorescent marker that is specific for cancer cells. More than one, but typically less than four, lymph nodes may be identified by this procedure as the "sentinel" lymph node.

Thus, there exists a need for agents and instruments that can be used for the diagnosis, prognosis, and removal of cancer tissue or cells to improve patient disease outcomes.

BRIEF SUMMARY OF THE INVENTION

Detection and removal apparatuses are described that may be used to detect, manipulate and/or remove fluorescent, phosphorescent or luminescent compounds or tissues in a sample. According to one example of an embodiment, the apparatus includes a light-emitting component, a light-detecting component, a lock-in amplifier or lock-in frequency-specific detector circuit, a frequency generator that is linked to the lock-in amplifier or frequency-specific detector circuit and the light-emitting component, and may include a speaker or other sound transducer that is capable of emitting sound that is perceptible by humans, and wherein the output audio signal or sound varies in strength, pitch, or phase with the intensity of the detected fluorescence in the sample. The apparatus may also include a visible output or graphical depiction of relative fluorescent intensity where the visible output varies in strength, in number, in magnitude, in shape, or in configuration as the intensity of the detected fluorescence in the sample changes. The apparatus may also include a mechanical signal such as a vibrating human interface or "stick shaker" that signals the operator that emitted light or the absence of emitted light has been detected. The apparatus may also include one or more focusing lenses, fiber-optic cables, lightguides, liquid lightguides, or mirrors, or one or more optical filters such as a long-pass filter, short-pass filter, interference filter, notch filter, holographic notch filter, absorptive neutral density filter, reflective neutral density filter, or infrared filter. The apparatus may also include an adjustable or fixed time delay between the excitation pulse or signal and the detection of an emitted light signal to enable the detection of time-delayed fluorescence, phosphorescence, or luminescence.

According to another example of an embodiment, the apparatus includes a light-emitting component, a light-detecting-component, a lock-in amplifier, a frequency generator that is operatively linked to the lock-in amplifier and the light-emitting component, and a laser that is operatively coupled to the lock-in amplifier through a control switch. The apparatus may also include one or more focusing lenses, fiber-optic cables, lightguides, liquid lightguides, or mirrors, or one or more optical filters such as a long-pass filter, short-pass filter, interference filter, notch filter, holographic notch filter, absorptive neutral density filter, reflective neutral density filter, or infrared filter. The apparatus may also include an adjustable or fixed time delay between the excitation pulse or signal and the detection of an emitted light signal to enable the detection of time-delayed fluorescence, phosphorescence, or luminescence.

According to one embodiment, fluorescent cobalamins comprised of a fluorescent, phosphorescent, luminescent or light-producing compound that is covalently linked to cobalamin can be used in conjunction with the above-described apparatuses. These fluorescent cobalamins can be used as a diagnostic and prognostic marker (a) to distinguish cancer cells and tissues from healthy cells and tissues, including identifying lymph nodes that contain cancer cells, (b) to determine if an individual will respond positively to chemotherapy using cobalamin-therapeutic bioconjugates, and (c) to facilitate or cause the direct removal or destruction of cells containing an increased concentration of the fluorescent analogue cobalamins. The fluorescent cobalamin analogues offer the properties of (1) rapid transport and storage by cancer cells (maximum uptake occurs at 4-96 hours), (2) a bright fluorophore, phosphorophore, or luminescent complex that can be visually detected at very low concentrations, and (3) nontoxic components.

In one aspect, fluorescent cobalamins are provided in which fluorescent, phosphorescent, luminescent or light-producing compounds are covalently linked to cobalamin (vitamin $B_{12}$). The fluorescent, phosphorescent or light-producing compounds can be covalently linked to the cobalt atom, the corrin ring, the ribose moiety of cobalamin, or one of the sidechain amides of the corrin ring after hydrolysis to the corresponding carboxylic acid. It is currently preferred to covalently link the fluorescent, phosphorescent, luminescent or light-producing compound to the cobalt atom, the corrin ring or the ribose moiety. Although any fluorescent, phosphorescent, luminescent or light-producing compound can be utilized in preparing the fluorescent cobalamins, it is currently preferred to utilize fluorescent, phosphorescent, luminescent or light-producing compounds that are excitable with ultraviolet, visible or infrared light. Examples of currently preferred fluorescent compounds include, but are not limited to, cobalafluors, fluorescein, fluorescein-SEX, methoxycoumarin, naphthofluorescein, BODIPY 493/503, BODIPY FL, BODIPY R6G, BODIPY 530/550, BODIPY TMR, BODIPY 564/570, BODIPY 576/589, BODIPY 581/591, BODIPY TR, Cascade Blue, Dansyl, Dialkylaminocoumarin, 4',5'-dichloro-2',7'-dimethyoxyfluorescein 2',7'-dichlorofluorescein, eosin, eosin F3S, erythrosin, hydroxycoumarin, lissamine rhodamine B, NBD, Oregon Green 488, Oregon Green 500, Oregon Green 514, PyMPO, pyrene, rhodamine 6G, rhodamine green, rhodamine red, rhodol green, 2',4',5',7'-tetrabromosulfonefluorescein, tetramethylrhodamine (TMR), Texas Red, X-rhodamine, Cy2 dye, Cy3 dye, Cy5 dye, Cy5.5 dye, Cy7 dye, IC Green, a chelating moiety that binds a lanthanide ion, or a quantum dot structure. The currently preferred fluorescent cobalamins fluoresce when excited by ultraviolet, visible or infrared light without the need to separate the fluorescent or phosphorescent compound from cobalamin. The light may be provided by an arc lamp, a hot filament emitter, a laser, a light-emitting diode, or a fiber-optic light source with appropriate filter.

In a second aspect, the fluorescent cobalamins are used to identify atypical cells such as neoplastic cells, dysplastic cells, or hyperplastic cells. More particularly, the fluorescent cobalamins are used to distinguish cancer cells from healthy cells. In one embodiment, a fluorescent cobalamin is administered to a patient prior to, or during, surgery. The presence of fluorescence, phosphorescence, luminescence or emitted light in cancer cells is used by the surgeon to define the tissue to be removed, whether in a primary tumor or in a metastatic site. In a second embodiment, a fluorescent cobalamin is administered to a patient in a manner suitable for uptake by lymph nodes that drain the situs of the tumor. The presence of fluorescence, phosphorescence, luminescence or emitted light identifies those lymph nodes that should be removed during surgery. In this latter embodiment, laparoscopic, endoscopic and microscopic techniques can be utilized to identify lymph nodes with cancer cells. The use of these techniques facilitates the identification and retrieval of positive lymph nodes.

In a third aspect, the fluorescent cobalamins are used to determine if an individual will respond positively to chemotherapy using cobalamin-based therapeutic bioconjugates. In this aspect, a fluorescent cobalamin is used to assess the ability of the particular cancer cell type to transport and store cobalamin, both qualitatively and quantitatively. Various types of cancer that transport and store large amounts of cobalamin are good candidates for therapy with cobalamin-based therapeutic bioconjugates. Quantification of tumor cell cobalamin binding, uptake; transport, and storage can be carried out by fluorescence under visual inspection (e.g., tissue slide), by epifluorescence microscopy, fluorescence laparoscopy, fluorescence endoscopy or flow cytometry.

In a fourth aspect, the fluorescent cobalamins are used to determine the levels of cobalamin in blood, plasma, serum, cerebrospinal fluid or urine or to determine the amount of unbound cobalamin binding capacity in blood, plasma, serum or cerebrospinal fluid.

In a fifth aspect, any fluorescent molecule (cancer-targeted or non-targeted) can be detected in a lymph node using the above-described apparatuses.

A sixth aspect comprises a method of detecting the location of fluorescent material in a sample using the above-described apparatuses. The sample may be biological tissue and the fluorescent material may be located preferentially in cancerous, neoplastic, dysplastic, or hyperplastic tissue. Alternatively, the fluorescent material is located preferentially in surrounding or structurally integrated non-cancerous, non-neoplastic, non-dysplastic, or non-hyperplastic tissue.

A seventh aspect comprises a method of removing fluorescent material in a sample using the above-described apparatuses. The sample may be biological tissue and the fluorescent material may be located preferentially in cancerous, neoplastic, dysplastic, or hyperplastic tissue. Alternatively, the fluorescent material is located preferentially in non-cancerous, non-neoplastic, non-dysplastic, or non-hyperplastic tissue.

An eighth aspect comprises a method of removing non-fluorescent material in a sample using the above-described apparatuses. The sample may be biological tissue and the fluorescent material may be located preferentially in cancerous, neoplastic, dysplastic, or hyperplastic tissue. Alternatively, the fluorescent material is located preferentially in surrounding or structurally integrated non-cancerous, non-neoplastic, non-dysplastic, or non-hyperplastic tissue.

A ninth aspect comprises a method of removing cancerous, neoplastic, dysplastic, or hyperplastic tissue from a subject, the method comprising: providing to the subject a fluorescent dye that preferentially localizes to cancerous, neoplastic, dysplastic, or hyperplastic tissue, detecting the level of relative fluorescent intensity in the subject, and laser ablating the tissue in which the relative fluorescent intensity indicates the preferential localization of the fluorescent dye.

BRIEF DESCRIPTION OF THE SEVERAL VIEWS OF THE DRAWINGS

It will be appreciated by those of ordinary skill in the art that the elements depicted in the various drawings are not to scale, but are for illustrative purposes only. The nature of the present invention, as well as other embodiments of the present invention, may be more clearly understood by reference to the following detailed description of the invention, to the appended claims, and to the several drawings, wherein:

DETAILED DESCRIPTION OF THE INVENTION

The present invention relates generally to systems for detection and removal using fluorescent, phosphorescent, or emitted light.

Figure 1:
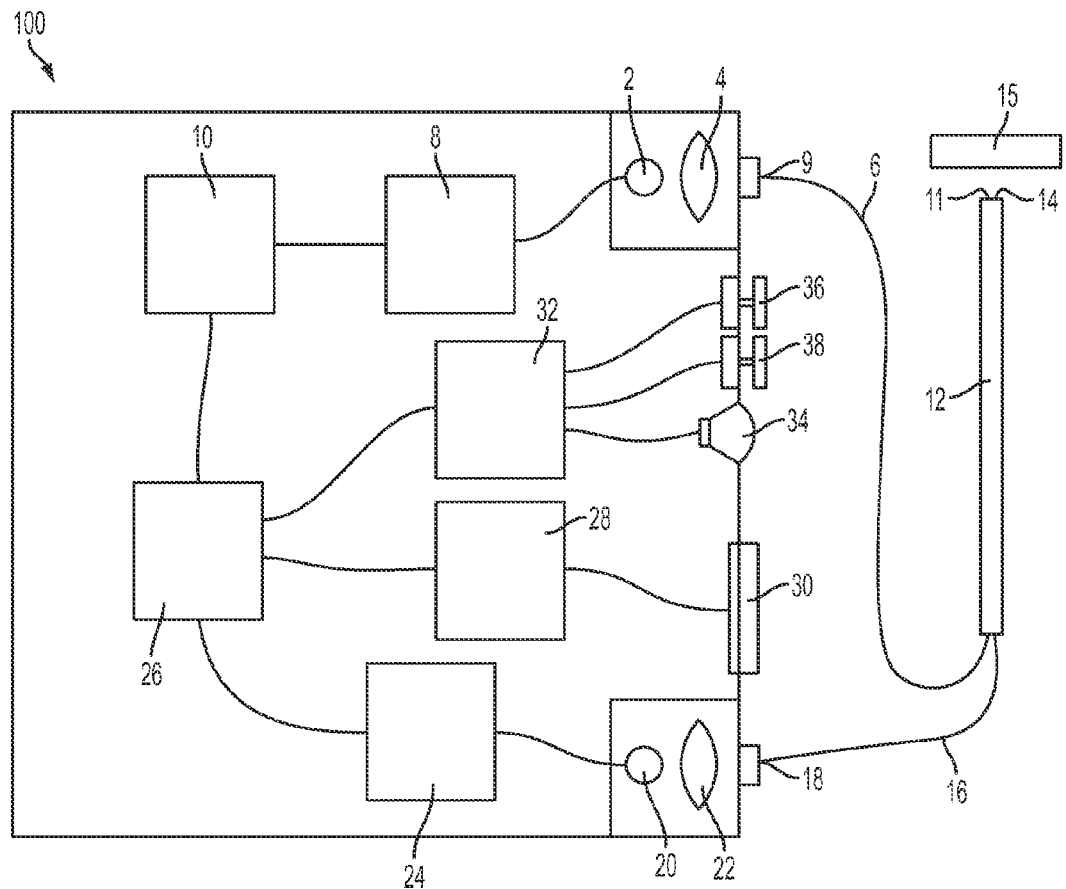
FIG. 1 shows a schematic diagram of an apparatus used to localize fluorescent material in a sample in accordance with one embodiment of the present invention.

Referring now to drawing FIG. 1, there is illustrated a schematic view of one example of an embodiment of an apparatus 100 according to the present invention. As illustrated, the apparatus 100 includes light-emitting component 2 that is used to generate light capable of stimulating a fluorescent, phosphorescent, or luminescent emission from a target light-emitting material. The emission of light by light-emitting component 2 is controlled by driver 8, which is configured to control the flow of electrical power to light-emitting component 2. In this way, driver 8 controls when light-emitting component 2 is providing light to excitation optical fiber 6. Driver 8 is in turn controlled by frequency generator 10. Frequency generator 10 controls the illumination of light-emitting component 2 through driver 8, resulting in the modulation or periodic strobing of the light emitted by light-emitting component 2 at a frequency determined by the frequency generator 10.

The modulated or periodically strobed light from light-emitting component 2 is at least one excitation fiber coupled to the light-emitting component 2. At least one receiving fiber coupled to the light-detecting component is transmitted to the proximal end 9, of excitation optical fiber 6, which transmits the strobed light down the length of the excitation optical fiber 6 in such a manner as to allow the modulated or periodically strobed light to be emitted from the terminal end 11 of the excitation optical fiber 6. Further, the strobed light may optionally pass through a filter 4, which may define or limit the wavelength(s) of light that are transmitted to excitation optical fiber 6. As can be seen in FIG. 1, the terminal end 11 of excitation optical fiber 6 may be encased in or otherwise coupled to a probe 12 so as to aid an operator in controlling the location of the terminal end 11 of excitation optical fiber 6. The modulated or periodically strobed light that is emitted from the terminal end 11 of excitation optical fiber 6 may be used to illuminate sample 15. If sample 15 contains a light-emitting material that is capable of being stimulated by the wavelength of the strobed light, the light-emitting material will fluoresce, phosphoresce, or luminesce.

Fluorescent, phosphorescent, or luminescent light emitted by a light-emitting material present in sample 15 is captured by terminal end(s) 14 of one or more receiving optical fibers 16 and transmitted the length of the one or more receiving optical fibers 16 to the proximal end 18 of the one or more receiving optical fibers 16. As with the excitation optical fiber 6, the terminal end(s) 14 of the one or more receiving optical fibers 16 may be encased in probe 12 so as to aid an operator in controlling the location of the terminal end(s) 14 of the one or more receiving optical fibers 16. One or more focusing, collimating, and/or collecting lens(es) may be placed in front of the optical fiber probe to focus, gather, or otherwise direct the excitation and emitted light. The transmitted fluorescent, phosphorescent, or luminescent light is then emitted from the proximal end 18 of the one or more receiving fibers and is detected by a light-detecting component 20 that is positioned so as to be able to detect any light emitted from the terminal end 18 of the receiving fibers 16. Optionally, the fluorescent, phosphorescent, or luminescent light may pass through a filter 22, which may limit the wavelength(s) of light that are transmitted to light-detecting component 20.

Upon detection of the fluorescent, phosphorescent, or luminescent light by light-detecting component 20, a signal is created that is proportional in strength to the intensity of light detected by the light-detecting component 20. The signal may be transmitted to amplifier 24 where the signal is boosted. From amplifier 24, the signal may be transmitted to lock-in amplifier 26. As will be appreciated by one of ordinary skill in the art, a lock-in amplifier may be used to measure the amplitude and phase of signals buried in noise. The noise in reference to the present invention includes any ambient illumination other than the fluorescent, phosphorescent, or luminescent light that may cause a signal to be produced by the light-detecting component 20. The frequency of incidence of the fluorescent, phosphorescent, or luminescent signal to be measured is set by a reference signal which is provided to the lock-in amplifier 26 by frequency generator 10. The lock-in amplifier 26 then removes the noise from the signal and generates a DC output signal equal in relative intensity to the fluorescent, phosphorescent, or luminescent light signal absent any noise from ambient illumination. Lock-in amplifiers are well known in the art and commercially available from various sources including, but not limited to, Boston Electric (Brookline, Mass.), Scitec Instruments (Cornwall, UK), Stanford Research Systems (Sunnyvale, Calif.), and Ametek Inc. (Paoli, Pa.). The DC output from lock-in amplifier 26 may be used, in part, to control a visual output driver 28, which, in turn, is used to produce a visible output of relative fluorescent, phosphorescent, or luminescent intensity 30. The visible output of relative fluorescent, phosphorescent, or luminescent intensity 30 provides the operator with a visual cue corresponding to the relative fluorescent, phosphorescent, or luminescent intensity emitted from sample 15. It is currently preferred that the visible output of relative fluorescent, phosphorescent, or luminescent intensity 30 be in the form of an LED bar graph, LED array, or display screen.

The DC output may also be used to drive a voltage controlled audio oscillator 32. The voltage controlled audio oscillator 32, in turn, controls a speaker 34 that serves to provide the operator with an audio cue corresponding to the relative fluorescent intensity emitted from sample 15. The output of the voltage controlled audio oscillator can be controlled by a user accessible volume control 36 and by a user accessible frequency control 38 that may be used to modulate the intensity or frequency of the sound generated by speaker 34. Currently preferred is a frequency of between about 100 Hz and about 20,000 Hz.

During normal operation, a strobed light is emitted from light-emitting component 2 with the frequency of the strobe being determined by driver 8 in conjunction with frequency generator 10. The strobed light is transmitted via excitation optical fiber 6 to sample 15 where any light-emitting material capable of being excited by the wavelength of the strobed light is made to fluoresce, phosphoresce, or luminesce. The fluorescent, phosphorescent, or luminescent light, along with any ambient light, is transmitted by the one or more receiving optical fibers 16 to light-detecting component 20. Light-detecting component 20 generates a signal whose intensity corresponds to the intensity of the illumination to which it is subject. The signal from light-detecting component 20 is then amplified by amplifier 24 and transmitted to lock-in amplifier 26. Lock-in amplifier 26, using an input from frequency generator 10, filters any noise due to ambient light and creates a DC output that corresponds in relative intensity to the level of fluorescent, phosphorescent, or luminescent light detected by light-detecting component 20. The DC output is then used to drive a visual signal, provided by visible output of relative fluorescent, phosphorescent, or luminescent intensity 30 as driven by the visual output driver 28, corresponding to relative fluorescent, phosphorescent, or luminescent intensity. Additionally, the DC output drives an audio signal, provided by speaker 34 as driven by voltage controlled audio oscillator 32, which also corresponds to relative fluorescent, phosphorescent, or luminescent intensity. The volume and frequency of the audio output may be modulated by user accessible volume control 36 and user accessible frequency control 38 respectively. Thus, in use, the apparatus 100 may be used by an operator to determine the location of any light-emitting material in a sample and to determine its margins through the use of the audio, visual, or mechanical cues provided in real time.

It will be appreciated by one of ordinary skill in the art that any type of light-emitting component 2 may be used so long as it provides a frequency of light capable of stimulating a fluorescent, phosphorescent, or luminescent emission from the light-emitting material. Examples of light-emitting components 2 suitable for use in the present invention, include, but are not limited to, lasers, laser diodes, light-emitting diodes, organic light-emitting diodes, fiber-optic light sources, luminous gas discharges, hot filament lamps, and similar light sources. Currently preferred is the use of a light-emitting diode or laser diode.

As will be additionally appreciated by one of ordinary skill in the art, sample 15 may be any kind of sample that can contain a light-emitting material. Examples of samples suitable for use with the present invention include, but are not limited to, tissue, biological tissue, and biological tissue comprising cancerous and/or neoplastic, dysplastic, or hyperplastic tissue.

As will be further appreciated by one of ordinary skill in the art, any type of light-emitting material may be used so long as the emitted fluorescent, phosphorescent, or luminescent light is detectable by light-detecting component 20. Examples of light-emitting materials suitable for use in conjunction with the present invention, include, but are not limited to, CobalaFluors, fluorescein, fluorescein-SEX, methoxycoumarin, naphthofluorescein, BODIPY 493/503, BODIPY FL, BODIPY R6G, BODIPY 530/550, BODIPY TMR, BODIPY 564/570, BODIPY 576/589, BODIPY 581/591, BODIPY TR, Cascade Blue, Dansyl, Dialkylaminocoumarin, 4',5'-dichloro-2',7'-dimethyoxyfluorescein, 2',7'-dichlorofluorescein, eosin, eosin F3S, erythrosin, hydroxycoumarin, lissamine rhodamine B, NBD, Oregon Green 488, Oregon Green 500, Oregon Green 514, PyMPO, pyrene, rhodamine 6G, rhodamine green, rhodamine red, rhodol green, 2',4',5',7'-tetrabromosulfonefluorescein, tetramethylrhodamine (TMR), Texas Red, X-rhodamine, Cy2 dye, Cy3 dye, Cy5 dye, Cy5.5 dye, Cy7 dye, IC Green, a chelate complex that binds a lanthanide metal ion, or a quantum dot structure.

As will be additionally appreciated by one of ordinary skill in the art, any type of filter 4 or filter 22 may be used such that the filter has the capability to remove, block, absorb, reflect, or deflect a portion of the light passing therethrough. Examples of filters suitable for use in the present invention, include, but are not limited to, notch filters, holographic notch filters, long-pass filters, short-pass filters, interference filters, absorptive neutral density filters, reflective neutral density filters, infrared filters, prisms, gratings, and mirrors.

As will be additionally appreciated by one of ordinary skill in the art, an apparatus according to the present invention may also include an adjustable amount of fixed time delay between the excitation pulse and the detection of an emitted light signal to enable the detection of delay fluorescence, phosphorescence, or luminescence.

As will be appreciated by one of ordinary skill in the art, excitation optical fiber 6 and the one or more receiving fibers 16 may be any type of flexible fiber useful for transmitting light. Examples of such fibers include, but are not limited to, endglow, stranded, jacketed, and unjacketed fiber-optic cables, lightguides, and liquid lightguides.

As will be further appreciated by one of ordinary skill in the art, light-detecting component 20 may be any type of light-detecting component capable of generating a signal whose intensity varies with the intensity of light incident upon the light-detecting component. Examples of light-detecting components suitable for use in the present invention include, but are not limited to, p-n photodiodes, p-i-n photodiodes, photomultiplier tubes, and avalanche photodiodes.

As will be appreciated by one of ordinary skill in the art, a wide range of user accessible controls may be used to adjust volume, frequency, or signal threshold. Examples of controls suitable for use in the present invention include, but are not limited to, knobs, switches, digital controls, buttons, touch-screen controls, or other devices that can be manipulated by a user. As will be further appreciated by one of ordinary skill in the art, the audio signal emitted by speaker should be humanly perceptible and may vary in conjunction with the magnitude of the fluorescent, phosphorescent, or luminescent intensity by varying in strength, pitch, phase, or other humanly perceptible change. As will be yet further appreciated by one of ordinary skill in the art, the present invention is not limited to speakers per se, but any sound transducer capable of producing a humanly perceptible output may be used.

As will be appreciated by one of ordinary skill in the art, visible output of relative fluorescent, phosphorescent, or luminescent intensity 30 may be any sort of visual output that provides the operator with a visual cue corresponding to the relative fluorescent intensity emitted from sample 15. Examples of visible outputs 30 include, but are not limited to, LED bar graphs, graphical depictions, images on a screen such as an LCD screen or a cathode ray tube, scrolling images on a screen displaying relative fluorescent, phosphorescent, or luminescent intensity over time, dial gauges, or any other means for visually relating to an operator the relative fluorescent, phosphorescent, or luminescent intensity detected. Further, the intensity of the visible output may vary in for example, but not limited to, strength, number, magnitude, shape, or configuration as the magnitude of the detected fluorescence, phosphorescence, or luminescence changes. It is currently preferred that the visible output of relative fluorescent, phosphorescent, or luminescent intensity 30 be in the form of an LED bar graph.

As will be additionally appreciated by one of ordinary skill in the art, probe 12 may be any kind of probe that can be controlled or manipulated by an operator. Examples of probes 12 that are suitable for use with the present invention, include, but are not limited to, hand-held probes, finger-tip mounted probes, surgical telescopes, endoscopes, cystoscopes, nephroscopes, bronchoscopes, laryngoscopes, otoscopes, arthroscopes, laparoscopes, colonoscopic endoscopes, and gastrointestinal endoscopes.

As will be appreciated by one of ordinary skill in the art, the probe 12 and any attendant fibers may be constructed so as to be easily removed and disconnected from the remainder of the apparatus. Such removability has the advantage of allowing the probe and/or attendant fibers to be sterilized or disposed of after it has been used.

As will be further appreciated by one of ordinary skill in the art, other signals may be provided to an operator that varies with the magnitude of the fluorescent, phosphorescent, or luminescent signal detected. For example, the apparatus may include a mechanical signal such as a vibrating human interface or "stick shaker" that signals the operator that emitted light or absence of emitted light has been detected.

Figure 2:
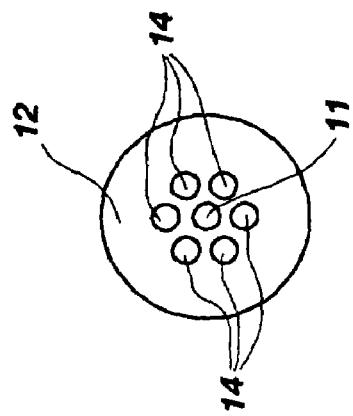
FIG. 2 illustrates one arrangement of fibers in a probe.

Referring now to drawing FIG. 2, there is illustrated an example of a terminal end view of a probe 12 showing one possible configuration of the terminal end 11 of excitation optical fiber 6 and the terminal ends 14 of six receiving fibers 16. As will be apparent to one of ordinary skill in the art, other configurations of excitation optical fiber 6 and one more receiving fibers within probe 12 are possible.

Figure 4:
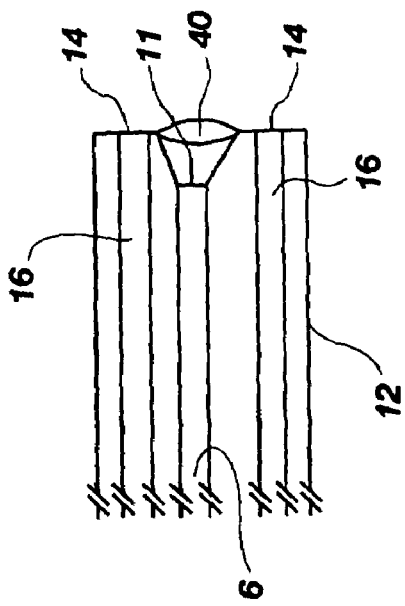
FIG. 4 illustrates a cutway view of the probe shown in FIG. 3 along plane A.
Figure 3:
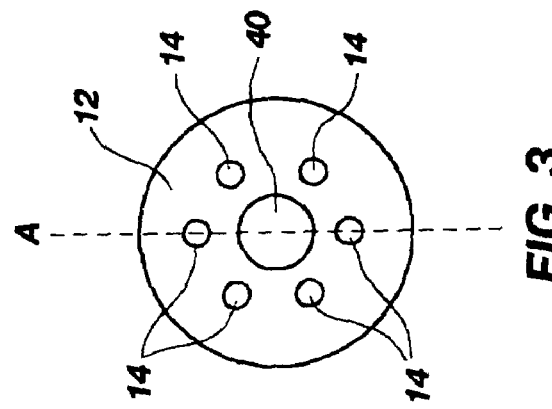
FIG. 3 illustrates a further arrangement of optical fibers in a probe including a lens for focusing excitation light.

Referring now to drawing FIG. 3, there is illustrated an exemplary embodiment of a probe 12 in which a focusing lens 40 is disposed terminal to the terminal end 11 of excitation optical fiber 6. The placement of focusing lens 40 is such that it is able to focus the light emitted from excitation optical fiber 6. Drawing FIG. 4, shows a cross section of probe 12 along plane A as illustrated in drawing FIG. 3.

Figure 5:
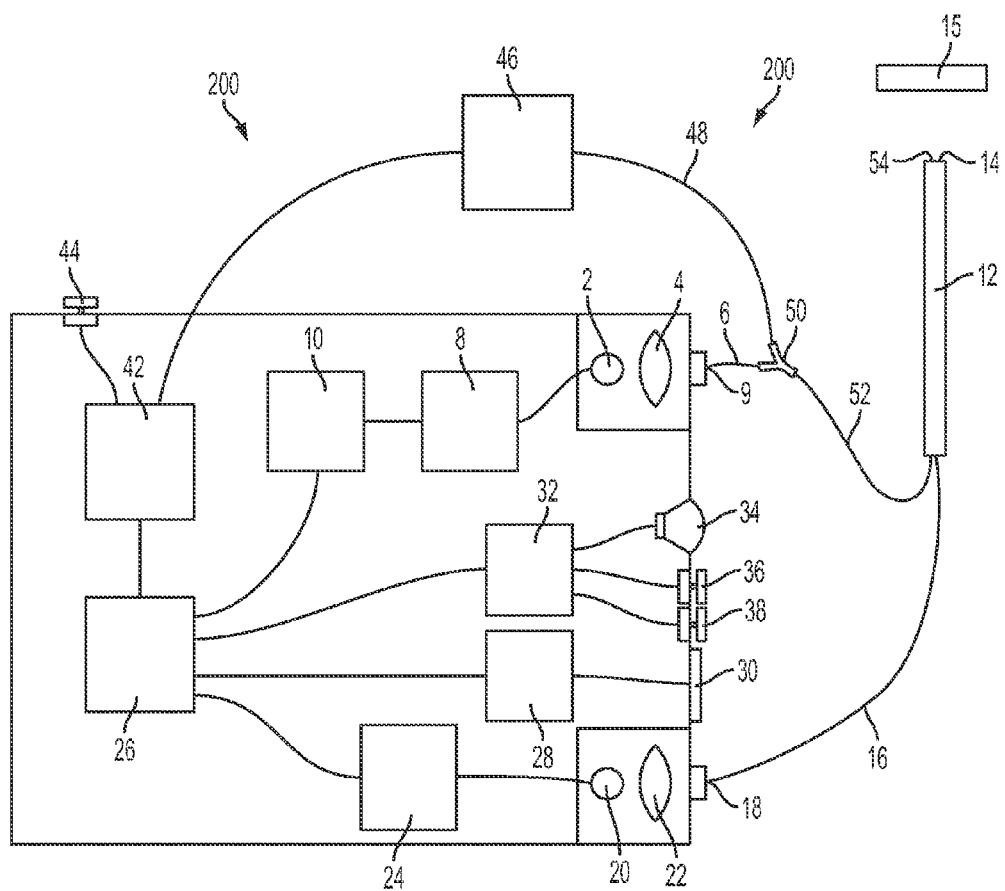
FIG. 5 shows a schematic diagram of an apparatus used to remove identified fluorescent or non-fluorescent material from a sample.

Referring now to drawing FIG. 5, there is illustrated a schematic view of a further example of an embodiment of an apparatus 200 according to the present invention. The apparatus contains many of the same parts as the apparatus illustrated in drawing FIG. 1, with the following additions. Further included in apparatus 200 is a control switch 42 that controls the operation of output device 46. Output device 46 is operably coupled with a transmission path 48 that facilitates the transmission of the output of output device to sample 15. In one embodiment, output device 46 may include a laser and transmission path 48 may include a laser fiber.

For the remainder of this description, without limiting the scope of the invention and for the purposes of illustration only, output device 46 will be referred to as laser 46 and transmission path 48 will be referred to as laser fiber 48. Control switch 42 is activated when a certain threshold level of voltage is supplied by lock-in amplifier 26. User accessible threshold control 44 may be utilized by a user to adjust the threshold DC output level from lock-in amplifier 26 such that the user can effectively define what level of fluorescent light detected by light-detecting component 20 triggers control switch 42 and, thus, actuates laser 46. Laser 46 provides a laser beam that travels down laser fiber 48 into y-junction 50. Y-junction 50 combines the light paths of excitation optical fiber 6 and laser fiber 48 into a single light path that passes into fiber 52. As can be seen in FIG. 5, the terminal end 54 of fiber 52 may be encased in or otherwise coupled to a probe 12 so as to aid an operator in controlling the location of the terminal end 54 of fiber 52.

During normal operation, a strobed light is emitted from light-emitting component 2 with the frequency of the strobe being determined by driver 8 in conjunction with frequency generator 10. The strobed light is transmitted via excitation optical fiber 6 to sample 15 where, for example, a fluorescent material capable of being excited by the wavelength of the strobed light is made to fluoresce. The fluorescent light, along with any ambient light, is transmitted by the one or more receiving fibers 16 to light-detecting component 20. Light-detecting component 20 generates a signal whose intensity corresponds to the intensity of the illumination to which it is subject. The signal from light-detecting component 20 is then amplified by amplifier 24 and transmitted to lock-in amplifier 26. Lock-in amplifier 26, using an input from frequency generator 10, filters any noise due to ambient light and creates a DC output that corresponds in relative intensity to the level of fluorescent light detected by light-detecting component 20. The DC output is then used to drive a visual signal, provided by visible output of relative fluorescent intensity 30 as driven by the visual output driver 28, corresponding to relative fluorescent intensity and an audio signal, provided by speaker 34 as driven by voltage controlled audio oscillator 32, which also corresponds to relative fluorescent intensity. The volume and frequency of the audio output may be modulated by user accessible volume control 36 and user accessible frequency control 38 respectively. The DC output of lock-in amplifier 26 is further provided to control switch 42. If the level of the DC output satisfies the threshold level defined by the user via user accessible threshold control 44, control switch 42 activates laser 46. Upon activation, laser 46 transmits a laser beam through laser fiber 48 and y-junction 50. Y junction 50 combines the laser beam with any strobed light provided by excitation optical fiber 6 such that all incoming light is passed into fiber 52. The laser beam emitted from the terminal end 54 of fiber 52 may be directed onto sample using a probe, such as probe 12 to ablate or otherwise destroy a selected portion of the sample 15. Thus, in use, the apparatus 200 may be used by an operator to ablate or cut a portion of a sample dependent on the relative fluorescent intensity of a particular portion of the sample.

It will be appreciated by one of ordinary skill in the art that any type of laser 46 that is capable of removing, ablating, or cutting a portion of the sample may be used. Examples of lasers 46 suitable for use in the present invention, include, but are not limited to, the surgical lasers commercially available from Lumenis Ltd. (Santa Clara, Calif.).

It will be further appreciated by one of ordinary skill in the art, that although a laser is illustrated herein as the output device capable of the removal or destruction of a portion of a sample, other devices or means for destruction or removal of a portion of a sample are contemplated within the scope of the invention. Other devices or means for the destruction or removal of a portion of a sample include, but are not limited to, electrocautery devices or scalpels, and ultrasonic cutters or ablators.

It will also be appreciated by one of ordinary skill in the art that the threshold used to activate the laser 46 may be a maximum or minimum threshold. For example, for a maximum threshold, the laser 46 is activated when the voltage provided by the lock-in amplifier 26 rises above the threshold. In the case of a minimum threshold, the ablative laser 46 is activated when the voltage provided by the lock-in amplifier 26 falls beneath the threshold.

Figure 6:
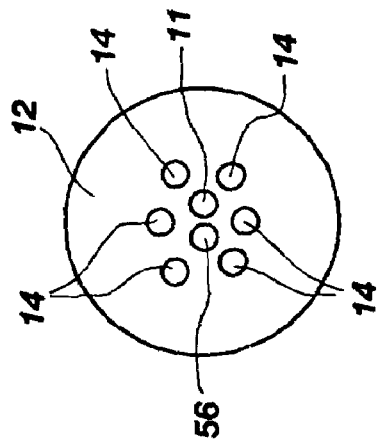
FIG. 6 illustrates a further arrangement of optical fibers in a probe.

It will be further appreciated by one of ordinary skill in the art that other methods of delivering the laser beam to the sample 15 may be used. For example, a separate fiber that is not joined to the excitation optical fiber 6 light path may be used to direct the laser onto the sample. Referring now to drawing FIG. 6, schematically illustrated therein is one possible embodiment of a probe 12 in which the light paths of laser fiber 48 and excitation optical fiber 6 are not joined but directed separately onto the sample 15. As illustrated therein, laser fiber 48 may have its own terminal end 56, that is placed adjacent to or nearby to the terminal end 11 of excitation optical fiber 6.

A further example of an embodiment according to the present invention comprises a method of detecting the presence and location of a light-emitting material in a sample. Light of a proper wavelength to stimulate the light-emitting material to produce fluorescent, phosphorescent, or luminescent light is directed onto a particular portion of the sample. Fluorescent, phosphorescent, or luminescent light emitted from that portion of the sample, if any, is collected and the intensity of the fluorescent, phosphorescent, or luminescent light is used to provide audio and visual cues to the practitioner of the method. In this manner, the practitioner of the method can distinguish between parts of sample that contain or do not contain a light-emitting material. Examples of apparatus suitable for the practice of this method are illustrated in drawings FIGS. 1 and 5. In a further example of a method according to the present invention, the sample may comprise biological tissue. In yet a further example, the fluorophore may be preferentially located in cancerous, neoplastic, dysplastic, or hyperplastic tissue. Thus, the practice of one example of a method according to the present invention enables a practitioner to distinguish between normal tissue and cancerous, neoplastic, dysplastic, or hyperplastic tissue.

A further example of an embodiment according to the present invention comprises a method of removing light-emitting material or non-light-emitting material from a sample. Light of a proper wavelength to stimulate the light-emitting material to produce fluorescent, phosphorescent, or luminescent light is directed onto a particular portion of the sample. Fluorescent, phosphorescent, or luminescent light emitted from that portion of the sample, if any, is collected and the intensity of the fluorescent, phosphorescent, or luminescent light, if beyond a predetermined user defined or otherwise established threshold, is used to activate a laser or other device that ablates or otherwise destroys the portion of the sample which is fluorescing. In this manner, the practitioner of the method can distinguish between parts of sample that contain or do not contain a light-emitting material and ablate or otherwise destroy portions of the sample, depending on the wishes of the operator, which do or do not emit a threshold level of fluorescent, phosphorescent, or luminescent light. Examples of apparatus suitable for the practice of this method are illustrated in drawing FIG. 5. In a further example of a method according to the present invention, the sample may comprise biological tissue. In yet a further example, the fluorophore may be preferentially located in cancerous, neoplastic, dysplastic, or hyperplastic tissue. Thus, the practice of one example of a method according to the present invention enables a practitioner to distinguish between normal tissue and cancerous, neoplastic, dysplastic, or hyperplastic tissue and to selectively remove or destroy portions of the sample as desired.

Any type of fluorescent, phosphorescent, or luminescent material could be used with the above-described devices. A particularly useful material is a fluorescent cobalamin that comprises a fluorescent compound (fluorophore), a phosphorescent compound (phosphorophore), a luminescent compound (chemiluminescent chromophore) or a light-producing compound that is covalently linked to cobalamin (vitamin $B_{12}$). These fluorescent cobalamins can be used as diagnostic and prognostic markers (a) to distinguish cancer cells and cancerous tissue from healthy cells and tissues, including identifying lymph nodes containing cancer cells, and (b) to determine if an individual will respond positively to chemotherapy using cobalamin-therapeutic bioconjugates.

The fluorescent cobalamins may be prepared by covalently attaching a fluorophore, a phosphorophore, chemiluminescent chromophore or a light-producing molecule to cobalamin. The fluorophore, phosphorophore, chemiluminescent chromophore or light-producing molecule is covalently linked to the cobalt atom, to the corrin ring or to the ribose sugar directly or via a linker molecule. The covalent linkage is preferably accomplished with the use of a linker molecule. If the fluorophore, phosphorophore, chemiluminescent chromophore or light-producing molecule is attached to the cobalt atom of cobalamin, the fluorescence, phoshorescence or emitted light is diminished in intensity through quenching by the spin of the cobalt atom. In addition, prolonged exposure of the fluorescent cobalamin to light will cleave the cobalt-carbon bond and release the fluorophore, phosphorophore, chemiluminescent chromophore or light-producing molecule from cobalamin. Thus, it is currently preferred to attach the fluorophore, phosphorophore, chemiluminescent chromophore or light-producing molecule to the corrin ring or the ribose moiety of the cobalamin molecule. These latter fluorescent cobalamins do not have the disadvantages of the fluorescent cobalamins in which the fluorophore, phosphorophore, chemiluminescent chromophore or light-producing molecule is covalently linked to the cobalt atom.

Attachment of the fluorophore, phosphorophore, luminescent chromophore, chemiluminescent chromophore or light-producing molecule to a carboxylate on the corrin ring or the 5'-ribose hydroxyl group circumvents the problem of lower sensitivity and photolability. In general, corrin ring carboxylate derivatives are known, but none of the compounds synthesized have contained a fluorescent marker. The fluorophore, phosphorophore, chemiluminescent chromophore or light-producing molecule can be attached directly to the corrin ring, rather than to the cobalt atom by derivatization of the cobalamin monocarboxylate according to published methods.

Although any fluorophore, phosphorophore, chemiluminescent chromophore or light-producing molecule can be utilized in preparing the fluorescent cobalamins, it is currently preferred to utilize fluorophores that are excitable with visible or infrared light. It is currently preferred to use visible or infrared light for in vivo use of the fluorescent cobalamins. Examples of currently preferred fluorophores include, but are not limited to, fluorescein, fluorescein-SEX, methoxycoumarin, naphthofluorescein, BODIPY 493/503, BODIPY FL, BODIPY R6G, BODIPY 530/550, BODIPY TMR, BODIPY 564/570, BODIPY 576/589, BODIPY 581/591, BODIPY TR, Cascade Blue, Dansyl, Dialkylaminocoumarin, 4',5'-dichloro-2',7'-dimethyoxyfluorescein, 2',7'-dichlorofluorescein, eosin, eosin F3S, erythrosin, hydroxycoumarin, lissamine rhodamine B, NBD, Oregon Green 488, Oregon Green 500, Oregon Green 514, PyMPO, pyrene rhilodamine 6G, rhodamine green, rhodamine red, rhodol green, 2',4',5',7'-tetrabromosulfonefluorescein, tetrametihylrhiodamine (IMR), Texas Red, X-rhodamine, Cy2 dye, Cy3 dye, Cy5 dye, Cy5.5 dye, Cy7 dye, IC Green, or a quantum dot structure. The currently preferred fluorescent cobalamins fluoresce when excited by visible or infrared light without the need to cleave the fluorophore from the bioconjugate. The light may be provided by a laser or a fiber-optic light source with an appropriate filter.

It has been found that there is differential uptake of fluorescent cobalamin analogues in normal and leukemic human bone marrow. The difference between normal marrow cells and leukemic myeloblasts (cancer cells) is particularly noteworthy, with no detectable cobalamin being taken up by normal cells. Bone marrow samples from healthy individuals show no fluorescent labeling. It has also been found that there is uptake of a doxorubicin-cobalamin conjugate, originally synthesized as a potential chemotherapeutic compound. Cellular uptake of the doxorubicin-cobalamin conjugate can be observed in P-388 murine leukemia cells, as well as in HCT-116 human colon tumor cells. Thus, the uptake of fluorescent derivatives of cobalamin occurs in leukemia and solid tumor cell lines. These results, in combination with the knowledge that all cancer cells increase cobalamin transport and storage, demonstrate the general applicability of the use of fluorescent cobalamins to distinguish cancer cells from normal cells.

Thus, the fluorescent cobalamins can be used, without limitation, to:

identify cancerous tissue visually, via fluorescence microscopy, fluorescence laparoscopy, fluorescence endoscopy, or flow cytometry;

identify cancerous cells in tissue sections or samples from tissue biopsies;

define tumor margins in vivo, ex vivo or in situ;

diagnose, detect, prognose, predict or monitor cancer in vivo, ex vivo or in situ;

identify metastatic cancer in vivo, ex vivo or in situ;

determine the stage of cancer progression;

identify cancer dermally or transdermally;

identify metastatic cancer dermally or transdermally;

identify cancer in lymph nodes, including in the sentinel lymph node or nodes or in an axillary lymph node or nodes, including with the use of minimally invasive techniques, such as laparoscopy or endoscopy;

identify metastatic disease in the treatment, detection, prediction, prognostication or monitoring of cancer, such as breast cancer, ovarian cancer, lung cancer, prostate cancer, epithelial cancer (adenocarcinoma), liver cancer, melanoma and lymphoma;

conduct flow cytometry studies of bone marrow aspirates or peripheral blood samples for diagnosing, predicting, prognosticating, monitoring or characterizing leukemia or lymphoma;

predict whether a patient will respond positively to chemotherapy that is based on the use of a cobalamin-therapeutic bioconjugate;

improve the definition of tumor micromargins in a biopsy or lumpectomy;

decrease the chance of leaving cancerous cells behind in a biopsy, lumpectomy, or tumorectomy and thereby reduce the need for follow-up surgery to remove the remaining cancer cells.

As used herein, prediction refers to understanding the biological behavior of the tumor, and how the tumor will respond (favorably or unfavorably) to therapy. Prognosis refers to the anticipated patient outcome following therapy (i.e., what is the likelihood of five- or ten-year survival following therapy). Monitoring refers to determining the success of therapy and detection of residual disease following treatment. An example is the use of a fluorescent cobalamin conjugate to test the bone marrow for the presence of myeloblasts following treatment of leukemia. Characterization refers to a descriptive or quantitative classification of the type of tumor in comparison to closely related types of tumors.

The fluorescent cobalamins can be administered in accordance with customary cancer diagnostic, detection, prediction, prognostication, monitoring or characterization methods known in the art. For example, the fluorescent cobalamins can be administered intravenously, intrathecally, intratumorally, intramuscularly, intralymphatically, or orally. Typically, an amount of the fluorescent cobalamin of the present invention will be admixed with a pharmaceutically acceptable carrier. The carrier may take a wide variety of forms depending on the form of preparation desired for administration, e.g., oral, parenteral, intravenous, intrathecal, intratumoral, circumitumoral, and epidural. The compositions may further contain antioxidizing agents, stabilizing agents, preservatives and the like. Examples of techniques and protocols can be found in *Remington's Pharmaceutical Sciences*. The amount of fluorescent cobalamin to be administered will typically be 1-500 mg.

As shown herein, cobalamin analogs are recognized by cobalamin transport proteins, such as haptocorrin (TCI or HC), intrinsic factor (IF) or transcobalamin (TCII), with high affinity. The attachment of large molecules to cobalamin does not appear to affect protein binding.

An improvement in the surgeon's ability to identify metastatic disease in lymph nodes will advance surgical therapy by, for example, preserving healthy tissue and minimizing the number of axillary lymph nodes removed. This will improve the patient's quality of life and improve morbidity and long-term mortality. Precise identification of cancer cells that have spread to lymph nodes will enable removal of only the diseased ducts and nodes, while sparing the healthy axillary nodes. With 186,000 new cases of breast cancer each year, the number of surgeries to remove primary tumors and determine the status of associated lymph nodes is significant. The perfunctory removal of all axillary lymph nodes and ducts leads to local edema and increased morbidity. The non-removal of axillary lymph nodes and ducts that contain metastatic cancer cells leads to decreased survival and increased long-term mortality.

In the sentinel lymph node biopsy approach, a blue dye and/or radioactive tracer are injected into the breast near the tumor. A small incision is made under the arm to look for traces of the dye or radioactivity to identify the lymph node(s) that drain the area of the breast and, as a consequence, are most likely to contain metastatic cancer cells. The above-described fluorescent cobalamin replaces the blue dye and radioisotope tracer currently used in sentinel lymph node biopsies. The use of the fluorescent cobalamins enables the application of the sentinel lymph node biopsy approach to all types of cancer. In addition, the fluorescent cobalamin enable the use of minimally invasive techniques, such as laparoscopic, endoscopic and microscopic techniques, in the analysis of cancer, especially the analysis of cancer cells in lymph nodes. The use of the fluorescent cobalamins will facilitate the identification and retrieval of positive lymph nodes. Thus, the fluorescent cobalamin can be used with the following cancers or cancers of: breast, skin (melanoma), gynecological (ovarian, prostate, uterine, cervical, vulval, penal, testicular), head and neck (lip, tongue, mouth, pharynx), digestive organs (esophageal, stomach, small intestine, large intestine, rectum, colon, liver, pancreas), bone, connective tissue, urinary organs (bladder, kidney), eye, brain and central nervous system, endocrine glands (thyroid), lymph tissues, Hodgkin's disease, non-Hodgkin's lymphoma and multiple myeloma.

In addition, the use of fluorescent cobalamins enables the use of minimally invasive techniques, such as laparoscopic and endoscopic techniques, for the identification of lymph nodes which contain cancer cells and which must be removed. The fluorescent cobalamins also may emit sufficiently bright light (e.g., bright blue in the case of CobalaFluor Y) that they can be visually detected with an unaided eye under white light. This proposed technology is designed to replace the two current methods of surgically examining the axillary lymph nodes in patients with operable breast cancer with a more accurate and less painful method. The two operations now in use are the standard axillary node dissection using a large incision (approximately 5 inches) and removing all of the lower level lymph nodes (10-15). The second, and currently experimental method, is the sentinel lymph node biopsy. This method uses either a visual dye or a gamma emitter to identify the first lymph node to drain the breast. This requires a similarly large incision and a technically challenging examination of the lymphatic pathways. The presently disclosed cobalamin molecules will take a photophore to the nodes with cancer. The lymph nodes are examined directly through three small incisions (3-5 mm) using laparoscopic instruments. The closed operative technique provides a dark field for laser excitation. The bright emission of stimulated light from the cobalamin-photophore conjugate in the tumor bearing lymph nodes will facilitate identification and retrieval of positive lymph nodes. This method will result in less dissection, less pain and better accuracy. Similar principles apply to using the fluorescent cobalamins to detect cancer cells with endoscopic techniques.

A further advantage of the fluorescent cobalamins is that they do not substantially pass through the lymphatic ducts. The two blue dyes conventionally used for sentinel lymph node procedures (Lymphazurine™ and methylene blue) tend to flow out of the lymphatic ducts into the surrounding tissue very quickly after they are injected into the tissue that drains the lymphatic ducts. Such leakage obscures the operative field with a generalized blue color.

Furthermore, since the fluorescent cobalamins are differentially taken up by cancer cells, these fluorescent cobalamins provide an improved marker that will enable surgeons to excise cancerous tissue selectively, thereby leaving healthy tissue.

The ability of fluorescent cobalamins bound to cancer cells to be detected laparoscopically or endoscopically demonstrates that fluorescent molecules can be used to determine a sentinel lymph node laparoscopically, endoscopically, or with an external probe. Thus, any fluorescent molecule (cancer-targeted or non-targeted) can be detected in a lymph node using laparoscopic or endoscopic visualization. As an example, a red fluorophore could be injected intratumorally as is now done in the sentinel lymph node procedure. Insufflation of the axilla would allow the surgeon to find the fluorescent node laparoscopically (through 2 small incisions) and thereby avoid the use of a non-cancer cell-specific radioactive tracer to help the surgeon find the general location of the sentinel node.

The fluorescent cobalamins offer several improvements as an intraoperative marker. These improvements include:

The fluorescent marker will be specific for cancer cells in lymph ducts and nodes, rather than simply indicating which node is draining the tidal basin. The fluorescent marker will also distinguish cancer cells from healthy cells.

The marker can be used in low concentrations because of the inherent sensitivity afforded by fluorescence detection. The blue dye now in use tends to obscure the active node and complicates postsurgical examination of the tissue by a pathologist. The blue dye also tends to obscure bleeding vessels, thereby complicating surgical excision of the node and subsequent wound closure. The use of a fluorescent marker should avoid these problems.

A fluorescent marker that is specific for cancer cells will improve the false-negative rate of 12% as is seen with the procedure as currently practiced.

A decreased false-negative rate should improve the acceptance of this technique by patients and surgeons. This might decrease the training time necessary (typically 30 or more cases with complete axial node dissection) for a surgeon to learn this procedure.

The fluorescent marker enables the use of laparoscopic, endoscopic and microscopic techniques for the visualization of cancer cells. These techniques can also be used to visualize primary tumors, metastatic tumors, axillary lymph nodes, inguinal lymph nodes and cervical lymph nodes. These techniques will reduce the necessity for large incisions and technically challenging examination of lymphatic pathways in the analysis of cancer. These techniques will result in less dissection, less pain and better accuracy.

The fluorescent cobalamins can also be used in a competitive binding assay to determine the concentration or amount of naturally occurring cobalamin (hydroxocobalamin, methylcobalamin, adenosylcobalamin, or cyanocobalamin) in blood, plasma, serum, or other bodily fluids. In this type of assay, a fluorescent cobalamin is used in place of radioactively labeled cobalamin in a competitive binding assay, well known to a skilled artisan. Radioactive assays for cobalamin have been described in U.S. Pat. Nos. 6,096,290; 5,614,394; 5,227,311; 5,187,107; 5,104,815; 4,680,273; 4,465,775; 4,355,018, among others, the disclosures of each of which is incorporated herein by reference. This assay procedure can be used to determine the amount of unsaturated cobalamin binding capacity in blood, plasma, serum, or bodily fluids, as well as the concentration of cobalamin that is bound to the proteins transcobalamin, haptocorrin, or intrinsic factor. The use of fluorescent cobalamins has a significant advantage over radioactively labeled cobalamin in a clinical chemistry binding assay because it does not require the special shipping, handling, and disposal procedures associated with radioactively labeled cobalamin.

It will be apparent to those of ordinary skill in the art that the embodiments described herein, while illustrative, are not intended to so limit the invention or the scope of the appended claims. Those of ordinary skill will understand that various combinations or modifications of the embodiments presented herein may be made without departing from the scope of the present invention. Thus, while certain exemplary embodiments and details have been described for the purposes of describing the invention, it will be apparent to those of ordinary skill in the art that various changes in the invention described herein may be made without departing from the scope of the present invention, which is defined in the appended claims.

What is claimed is:

1. An apparatus for detecting light-emitting material in a sample comprising:
    a light-emitting component;
    a light-detecting component for detecting fluorescence, phosphorescence or luminescence in the sample;
    a lock-in amplifier;
    a frequency generator operatively coupled to the lock-in amplifier and the light-emitting component;
    a driver controlled by the frequency generator and operatively coupled to the light-emitting component, wherein the driver is configured to control flow of electrical power to the light-emitting component;
    a sound transducer that is capable of emitting a humanly detectable signal wherein the signal varies with magnitude of detected fluorescence, phosphorescence or luminescence in the sample; and
    a visible output of relative fluorescent intensity where the visible output varies with the magnitude of the detected fluorescence, phosphorescence or luminescence in the sample.

2. The apparatus according to claim 1, wherein the light-emitting component is selected form the group consisting of lasers, laser diodes, light-emitting diodes, organic light-emitting diodes, fiber-optic light sources, luminous gas discharges, and hot filament lamps.

3. The apparatus according to claim 1, wherein the light-detecting component is selected form the group consisting of p-n photodiodes, p-i-n photodiodes, photomultiplier tubes, light-sensitive charge coupled devices, and avalanche photodiodes.

4. The apparatus according to claim 1, wherein the visible output of relative fluorescent, phosphorescent or luminescent intensity is selected form the group consisting of LEDs, LCDs, CRTs, plasma, and gauges.

5. The apparatus according to claim 1, further comprising a probe configured to be selectively coupled to the light-emitting component and/or the light-detecting component.

6. The apparatus according to claim 5, wherein the probe is selected from the group consisting of hand-held probes, finger-tip mounted probes, surgical telescopes, endoscopes, cystoscopes, nephroscopes, bronchoscopes, laryngoscopes, otoscopes, arthroscopes, laparoscopes, colonoscopic endoscopes, and gastrointestinal endoscopes.

7. The apparatus according to claim 5, wherein the probe further comprises at least one excitation fiber coupled to the light-emitting component and at least one receiving fiber coupled to the light-detecting component.

8. The apparatus according to claim 5, wherein the probe is sterilizable.

9. The apparatus according to claim 5, wherein the probe is disposable.

10. A system for the detecting light-emitting material in a sample comprising the apparatus of claim 1 and a light-emitting material, wherein the light-emitting material fluoresces, phosphoresces or luminesces upon stimulation by light from the light-emitting component.

11. A method of detecting the location of light-emitting material in a sample, the method comprising:
    using the apparatus of claim 1 to detect the location of light-emitting material in a sample.

12. The method according to claim 11, wherein the sample is biological tissue.

13. The method according to claim 12, where the light-emitting material, is located preferentially in cancerous, neoplastic, dysplastic, or hyperplastic tissue.

14. The method according to claim 11, where the light-emitting material is located preferentially in non-cancerous, non-neoplastic, non-dysplastic, or non-hyperplastic tissue.

* * * * *